United States Patent [19]

Beuving et al.

[11] Patent Number: 5,238,688
[45] Date of Patent: Aug. 24, 1993

[54] METHOD FOR PREPARING A POWDERED PARTICULATE COMPOSITION

[75] Inventors: Gerrit B. M. Beuving, Veghel; Henrik de Nijs, Oss, both of Netherlands

[73] Assignee: Akzo N.V., Velpeweg, Netherlands

[21] Appl. No.: 634,832

[22] Filed: Dec. 27, 1990

[30] Foreign Application Priority Data

Dec. 30, 1989 [NL] Netherlands ................. 8903199

[51] Int. Cl.$^5$ ............... A61K 9/14; A61K 31/55; A61K 9/16
[52] U.S. Cl. ................... 424/499; 424/487; 424/488; 424/501; 514/772.6; 514/781; 514/922; 514/974
[58] Field of Search ............ 424/81, 487, 488, 499, 424/501; 514/922, 974

[56] References Cited

U.S. PATENT DOCUMENTS

| | | | |
|---|---|---|---|
| 4,128,641 | 12/1978 | Itil | 514/250 |
| 4,284,559 | 8/1981 | van der Berg | 540/579 |
| 4,447,437 | 5/1984 | Ohnishi et al. | 514/284 |
| 4,623,588 | 11/1986 | Nuwayser et al. | 428/402.24 |
| 4,801,460 | 1/1989 | Goertz et al. | 424/465 |
| 4,834,985 | 5/1989 | Elger et al. | 424/488 |
| 4,870,060 | 9/1989 | Müller | 514/58 |
| 4,938,967 | 7/1990 | Newton et al. | 424/458 |

FOREIGN PATENT DOCUMENTS

0319061 6/1989 European Pat. Off. .
0320097 6/1989 European Pat. Off. .

OTHER PUBLICATIONS

Merck Index, 11th Ed, pp. 901, 1375, 769.

*Primary Examiner*—Thurman K. Page
*Assistant Examiner*—Edward J. Webman
*Attorney, Agent, or Firm*—William M. Blackstone

[57] ABSTRACT

Disclosed are powdered particulates or granules useful for the preparation of certain psychotropic compounds (e.g. mianserin are mirtazepine). The resulting suspensions and relatively tasteless, do not have a local anaesthetic effect and are easy to suspend. The granules contain the psychotropic compound, a cellulose derivative, polymer, and a filler.

8 Claims, No Drawings

METHOD FOR PREPARING A POWDERED PARTICULATE COMPOSITION

BACKGROUND OF THE INVENTION

1. Field

The present invention relates to granules, for oral administration in fluid form, of biologically active substances of the formula:

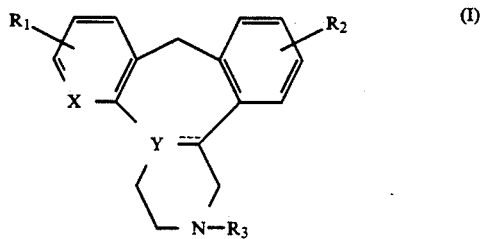

in which X=carbon or nitrogen,
Y=nitrogen or, if X is carbon, can also represent carbon,
$R_1$=H, OH, O-alkyl (1–4 C atoms), alkyl (1–4 C atoms) or a halogen,
$R_2$=H, OH, O-alkyl (1–4 C atoms), alkyl (1–4 C atoms) or a halogen,
$R_3$=H or alkyl (1–4 C atoms)
and the broken line indicates an extra bond which may or may not be present when Y is a carbon atom.

2. State of the art

Compounds of formula I are describe, inter alia, in U.S. Pat. Nos. 4,002,632 and 3,534,031. The form in which these compounds are used is generally the hydrochloride or other salt which is readily soluble in water.

In the case of orally administrable forms, these salts, which are readily soluble in water, have the problem that they have a very unpleasant taste and, moreover, have a local anaesthetic effect which is found to be particularly annoying.

In tablets, the unpleasant taste can be masked by adding auxiliaries; in the case of other oral administration forms this is found to be a problem which is difficult to solve.

The field of application of the compounds of formula I comprises, inter alia, a group of patients (e.g. elderly and disabled) for whom the tablet form is less suitable. For this group of patients an orally administrable fluid form would be very useful.

Because of the disadvantages outlined above, the readily soluble salts of the compounds of formula I cannot be used directly in a fluid administration form. In order to solve the problem, a suspension of an insoluble form of the active substance would have to be prepared.

In this context, the direct use of an insoluble form of the active substance, or the encapsulation of a readily soluble compound of formula I in a hydrophobic polymer, could be considered. However, the problem is then encountered that such substances are very difficult to suspend.

U.S. Pat. No. 4,447,437 discloses oral agents such as "granules". Oral agents according to that patent contain an active substance of formula I and pharmaceutically acceptable carriers or excipients. Examples of solid carriers and excipients include crystalline cellulose, cellulose derivatives, calcium carbohydroxycellulose, corn starch, potato starch, and mannitol.

European patent application 0,320,097 discloses the polymer Eudragit RS for use in a pharmaceutical preparation.

European patent application 0,319,061 to Akzo NV discloses an active substance of formula I in combination with Whitepsol 558, in a weight ratio of 1:100.

Problems which come to the fore with these preparations are: aggregation of the particles, settling of particles, and poor miscibility of the particles with water, as a result of which, when the particles are brought into suspension, some of the suspension will stick to the wall of the glass or plastic beaker and some will remain floating on the water surface. The dosage consequently becomes inaccurate.

The above problems can be reduced by adding surface-active substances. However, in view of possible side effects this is undesirable.

SUMMARY OF THE INVENTION

The invention provides a preparation for oral administration which is fluid or can easily be brought into fluid form, which is readily (re)suspendable, shows no aggregation or adhesion to walls, and does not produce an unpleasant taste and/or local anaesthetic effect.

The invention includes granules which contain
1) 1–5 parts by weight of a sparingly soluble form of a compound of formula I;
2) 0.3–3 parts by weight of a cellulose derivative which is soluble in water and in organic solvents;
3) 4–20 parts by weight of a pharmaceutically acceptable polymer which is insoluble in water; and
4) 40–250 parts by weight of a filler customary in pharmacy.

The granules according to the invention are simple to provide as such in sachets containing a suitable dosage. These granules are readily suspendable. Furthermore, an aqueous suspension which contains these granules can be chosen as the pharmaceutical form in place of the granules.

The granules according to the invention - introduced into a desired quantity of water and agitated - give readily drinkable, homogeneous, stable suspensions which do not have an unpleasant taste and show virtually no anaesthetic effect.

DESCRIPTION OF THE PREFERRED EMBODIMENTS

Preferably, the free base is chosen as the sparingly soluble form of the compounds of formula I. This has the advantage that the compound is rapidly converted in the stomach into the readily soluble hydrochlorides. It has been also found in the case of the free bases that the release from the granules is not delayed. This is one of the surprising aspects of the invention.

In the present invention a pharmaceutically acceptable polymer which is insoluble in water is understood to be a polymer which is swellable in water to a very small extent but cannot form a gel. The polymer is also soluble in organic solvents. Examples of such polymers include ethylene/vinyl acetate polymers with a high acetate content, polyethylene glycol esters and the like, and polyacrylates, such as the polymers which are available commercially under the trade name Eudragit, more particularly Eudragit RS.

A suitable polymer which is slightly permeable in water is a polymer sold under the Trade Mark EU- DRAGIT RS. EUDRAGIT polymers are polymeric lacquer substances based on acrylates and/or methacrylates. polymeric materials sold under the Trade Mark EUDRAGIT RS are acrylic resins comprising copolymers of acrylic and methacrylic acid esters with a low content of quaternary ammonium groups and are described in the "EUDRAGIT" brochure of Messrs. Rohm Pharma GmbH (1985) wherein detailed physical-chemical data of these products is given. The ammonium groups are present as salts and give rise to the permeability of the lacquer films. EUDRAGIT RS is slightly permeable, independent of pH.

A cellulose derivative which is soluble in water and organic solvents is preferably hydroxypropylcellulose, but other cellulose derivatives such as hydroxy-propylmethylcellulose and the like can also be used.

Reference should be made to the known pharmaceutical handbooks for the fillers customary in pharmacy. Very common fillers in this context are sorbitol, lactose and starch. Within the framework of the present invention, however, preference is given in particular to mannitol.

In addition to the aforementioned essential constituents, the granules according to the invention can also contain other auxiliaries customary in pharmacy, such as taste improvers, buffers which when introduced into water give a pH of 5-8, aroma substances and colorants.

Preferred granules according to the invention contain:
a) 2-3 parts by weight of a free base of formula I,
b) 8-15 parts by weight of an acrylate polymer which is available commercially under the name Eudragit RS,
c) 0.8-1.2 parts by weight of hydroxypropyl cellulose and
d) 80-150 parts by weight of mannitol.

The free base of formula I which is preferably used is mianserin ($R_1=R_2=H$, $R_3=CH_3$, $X=C$ and $Y=N$).

The granules according to the invention can be obtained using the mixing and granulating techniques customary in pharmacy. Preferably, however, components (1), (2) and (3) are dissolved in an organic solvent such as methanol, ethanol, acetone or methyl ethyl ketone, after which the solution obtained is added to component (4) and the mixture is granulated. The granules thus obtained, to which the abovementioned auxiliaries are also added if desired, are then sieved to the desired particle size.

The particle size of the composition according to the invention is not directly critical but nevertheless an average particle size of between 50 and 500 μm is desired. It is preferred that at least 75% of the composition have a particle size of approximately 100 to 300 μm.

The granules are preferably packaged in measured dosage units, for example in sachets or (non-consumable) capsules. Each dosage unit contains, for example, an amount of mianserin free base which corresponds to 10, 20, 30 or 60 mg of mianserin hydrochloride.

The invention is further explained by reference to the following illustrative examples.

EXAMPLE 1

Preparation of granules according to the invention containing 26.4 mg of mianserin free base per dose 100.0 grams of Eudragit RS, 10.0 grams of hydroxypropylcellulose and 26.4 grams of mianserin free base are dissolved successively in 160 millilitres of a mixture of acetone and ethanol (1:1, V:V). This solution is introduced onto 1113.6 grams of mannitol and the mixture is kneaded for 3 minutes in a rapid mixer (Gral, 10 litre). The mass is then sieved through a 2000 m sieve (Prewitt) and dried for 3 hours in a vacuum drying oven (Marius) at 50° C. under vacuum. The dried granules are then screened in two steps to a particle size of less than 300 μm (Prewitt). Each sachet is filled with 1.25 grams of these granules.

| A sachet then contains: | |
|---|---|
| Mianserin free base | 26.4 mg |
| Eudragit RS | 100.0 mg |
| Hydroxypropylcellulose | 10.0 mg |
| Mannitol | 1113.6 mg |
| Total | 1250.0 mg |

EXAMPLE 2

Preparation of a composition according to the invention containing 30 mg of mirtazapin ($X=N$, $Y=N$, $R_1=H$, $R_2=H$ and $R_3=CH_3$) per dose 80.0 grams of Eudragit RS, 8.0 grams of - hydroxypropylcellulose and 24.0 grams of mirtazapin (CAS-61337-67-5) are dissolved successively in 125 millilitres of a mixture of ethanol and acetone (1:1 V/V). This solution is introduced onto 888.0 grams of mannitol and the mixture is kneaded for 3 minutes in a rapid mixer (Gral, 10 litre). The mass is sieved through a 2000 μm sieve (Erweka). The mass is dried in a vacuum drying oven (Marius) for 3 hours at 50° C. under vacuum.

The granules are screened in two steps to a particle size which is smaller than 300 μm (Erweka). Each sachet is then filled with 1.25 grams of these granules.

| One sachet then contains: | |
|---|---|
| Mirtazapin | 30.0 mg |
| Eudragit RS | 100.0 mg |
| Hydroxypropylcellulose | 10.0 mg |
| Mannitol | 1110.0 mg |
| Total | 1250.0 mg |

We claim:

1. A process of manufacturing a powdered particulate comprising: dissolving
(a) 1-5 parts by weight of the free base of a compound of the formula:

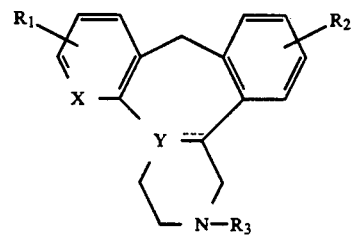

in which X=carbon or nitrogen, Y=carbon or nitrogen, $R_1$ and $R_2$ are each independently selected from H, OH, O-alkyl (1-4 C atoms), alkyl (1-4 C atoms) and a halogen, $R_3=H$ or alkyl (1-4 C atoms), and the broken line indicates an extra bond that may be present when Y is a carbon atom,
(b) 0.3-3 parts by weight of a cellulose derivative that is soluble in water and organic solvents, and (c) 4–20 parts by weight of a water insoluble pharmaceutically acceptable polymer in an organic solvent; and mixing with the solution formed (d) 40–250 parts by weight of a pharmaceutical filler distinct from said cellulose derivative and also distinct from said water insoluble pharmaceutically acceptable polymer and granulating said mixture, wherein the amount of organic solvent used is an amount of solvent effective for dissolving the compound, cellulose derivative and polymer and for granulating the solution formed with the pharmaceutical filler.

2. A process of manufacturing according to claim 1 further comprising screening the granules obtained to select a particle size of between 100 and 300 μm.

3. A process of manufacturing according to claim 1 further comprising screening the granules obtained to select a particle size of between 50 and 500 μm.

4. The process of manufacturing according to claim 1, wherein an acrylate polymer insoluble in water is used as the water insoluble pharmaceutically acceptable polymer.

5. The process of manufacturing according to claim 1, wherein the cellulose derivative is hydroxypropylcellulose.

6. The process of manufacturing according to claim 1, wherein mannitol is used as the filler.

7. The process of manufacturing according to claim 1, wherein the resulting powdered particulate comprises:

a) 2–3 parts by weight of said free base,
b) 8–15 parts by weight of an acrylic resin, comprising copolymers of acrylic and methacrylic acid esters, that is slightly permeable to water,
c) 0.8–1.2 parts by weight of hydroxypropylcellulose, and
d) 80–150 parts by weight of mannitol.

8. The process of manufacturing according to claim 1, wherein the free base is mianserin.

* * * * *